United States Patent [19]

Davis

[11] Patent Number: 5,585,375
[45] Date of Patent: Dec. 17, 1996

[54] METHOD FOR ALLEVIATING JET LAG

[76] Inventor: Bonnie M. Davis, 17 Seacrest Dr., Huntington, N.Y. 11743

[21] Appl. No.: 269,821

[22] Filed: Jul. 1, 1994

[51] Int. Cl.⁶ .................................................. A61K 31/55
[52] U.S. Cl. ............................................................ 514/215
[58] Field of Search ............................................. 514/215

[56] References Cited

U.S. PATENT DOCUMENTS 5,312,817  5/1994  Snorrason ................................ 514/141

OTHER PUBLICATIONS

Webster's II New Riverside University Dictionary, Riverside Publishing Co., Boston (1988), p. 653.
Riemann et al., *Psych. Res.*, 51(3), pp. 253–267 (1994).

*Primary Examiner*—Gary Geist
*Assistant Examiner*—Barbara S. Frazier
*Attorney, Agent, or Firm*—Ladas & Parry

[57] ABSTRACT

Jet lag and other upheavals of the body's internal clock may be alleviated by administering galanthamine to a person suffering such an upheavals prior to or just after such upheavals.

7 Claims, No Drawings

METHOD FOR ALLEVIATING JET LAG

GENERAL FIELD OF THE INVENTION

The present invention relates to a method for alleviating the effects of jet-lag or otherwise resetting the body's internal clock.

BACKGROUND OF THE INVENTION

Acetyl choline levels in the brain are known to be higher in animals that are awake than those who are sleeping. (see for example Saito et al Life Sci (Jan. 15, 1975, 16 (2): 281–8 and Zatz et al, Brain Res (May 11, 1981 212(1): 234–8). It has also been reported that when brain acetyl choline in rats was depleted their diurnal activity cycle was disrupted (Szymusia et al Brain Res Nov. 26, 1993 629 (10): 141–5. Furthermore chemicals that interfere with cholinesterase mechanisms are known to promote REM sleep over slow wave sleep (see for example a review by J. Valazquez—Moctezuma et al in S. M. Aquilonius and P. G. Gilberg (Eds) Progress in Brain Research, Vol. 84 1990 Elsevier Science Publishers 8V.. N.Y. pp. 407–413. Galanthamine is a known acetyl cholinesterase inhibitor. Such inhibitors act to reduce the rate at which acetyl choline is removed from a locus by the action of acetyl cholinesterase and thus may increase the local concentrations of acetyl choline in regions from which it would otherwise be removed by the cholinesterase. Galanthamine has been used for many years in eastern Europe as a recovery agent for use after anaesthesia and has recently been subject to clinical testing in Europe as a possible treatment for Alzheimer's Disease. (see also U.S. Pat. No. 4,663,318 B. Davis, May 5, 1987). Other recent suggestions for its use have been in connection with treatment of male erectile impotence (see U.S. Pat. No. 5,177,070 R. Katz Jan. 5, 1993) and in treatment of chronic fatigue syndrome (see U.S. Pat. No. 5,312,817 E. Snorrason, May 17, 1994).

BRIEF DESCRIPTION OF THE INVENTION

The present invention provides a method for alleviating the effects of jet lag which comprises administering to a traveller an alertness increasing amount of galanthamine at a time between 4 am and 3 pm of the time zone to which the traveller is about to travel is travelling or in which he has recently arrived.

In a second embodiment the present invention comprises administering galanthamine in a suitable dose to any one who requires a resetting of the internal clock—for example shift workers changing from a day to a night shift or vice versa.

DETAILED DESCRIPTION OF THE INVENTION

Galanthamine is a reversible acetylcholinesterase inhibitor that passes readily into the brain and has a relatively short half life in the body. Thus by taking an effective amount of galanthamine early in the day either just prior to (for example daily for up to a week prior to travel or soon after arriving in a new time zone, or otherwise adopting a new wake/sleep cycle one can reverse the effects of cholinesterase inhibition and increase the amount of acetyl choline in the brain and so alleviate the unpleasant effects of having to cope with a new day at a time when acetyl choline levels in the brain are still at their low night-time levels. Galanthamine should therefore be taken as early in the "day" (i.e. the period in which one wishes to be awake) as possible in order to maximize its effect and in any case should not be taken any later than eight hours prior to the time at which sleep is desired in the new time zone or new other sleep/wake cycle. Typically for treatment of jet lag the daily dose of galanthamine will be in the form of two doses one early in the morning and the other about lunch time. For many people it is desirable that galanthamine is taken together with food. Taking galanthamine in this manner for periods of up to one week (typically two or three days) before and/or after arrival in a new time zone should help to reset the travellers body clock and thus improve his or her ability to function more effectively than would otherwise be the case.

Suitable doses for this effect are in the range 5 to 45 mg, preferably in the range 10 to 35 mg. The best dose may vary depending upon the metabolism of the traveller the number of time zones through which the traveller has passed and the exact time at which the dose is administered, for example for many people the best dose may be about 15 to 25 mg per day. Galanthamine, like most cholinesterase inhibitors, may have side effects in some individuals and repeated dosing for more than a few days is normally to be avoided in the relatively young, particularly females of child-bearing age.

Most conveniently galanthamine may be administered for the purposes of the present invention in the form of tablets, although other conventional forms of providing oral doses such as capsules and caplets may also be used if desired. Most conveniently galanthamine is administered in the form of its hydrobromide salt although other acid addition form salts may also be employed.

I claim:

1. A method for alleviating the physiological effects of jet lag by resetting the internal clock of a traveller which comprises administering to a traveller from 5 to 45 mg of galanthamine at a time between 4 am and 3 pm of the time zone to which the traveller is about to travel, is travelling or in which he has recently arrived.

2. A method according to claim 1 wherein the administration of galanthamine is effected in a period of from one week before to one week after arrival in a new time zone.

3. A method according to claim 1 wherein galanthamine is administered at a time between 7 am and 12 noon of the time zone to which the traveller is travelling or in which he or she has recently arrived.

4. A method according to claim 1 wherein galanthamine is administered in the form of its hydrobromide.

5. A method according to claim 1 wherein the daily dose of galanthamine is in the range 10 to 30 mg.

6. A method according to claim 1 wherein the daily dose of galanthamine is in the range 20 to 25 mg.

7. A method of resetting the internal clock of one who has need thereof which comprises administering an effective dose of galanthamine to one who wishes to reset his or her wake-sleep cycle daily for at least three days, each administration being at least 8 hours prior to the time at which sleep is desired on the new cycle.

* * * * *